US012774454B2

(12) United States Patent
Tournier

(10) Patent No.: US 12,774,454 B2
(45) Date of Patent: Oct. 27, 2026

(54) ESTERASES AND USES THEREOF

(71) Applicant: CARBIOS, Clermont-Ferrand (FR)

(72) Inventor: Vincent Tournier, Toulouse (FR)

(73) Assignee: CARBIOS, Clermont-Ferrand (FR)

( * ) Notice: Subject to any disclaimer, the term of this patent is extended or adjusted under 35 U.S.C. 154(b) by 564 days.

(21) Appl. No.: 18/034,077

(22) PCT Filed: Oct. 27, 2021

(86) PCT No.: PCT/EP2021/079779
§ 371 (c)(1),
(2) Date: Apr. 27, 2023

(87) PCT Pub. No.: WO2022/090289
PCT Pub. Date: May 5, 2022

(65) Prior Publication Data

US 2023/0399629 A1 Dec. 14, 2023

(30) Foreign Application Priority Data

Oct. 27, 2020 (EP) .................................... 20306285

(51) Int. Cl.
*C12N 9/18* (2006.01)
*C08J 11/10* (2006.01)
*C11D 3/386* (2006.01)

(52) U.S. Cl.
CPC ............... *C12N 9/18* (2013.01); *C08J 11/105* (2013.01); *C11D 3/38636* (2013.01); *C12Y 301/01074* (2013.01); *C08J 2367/02* (2013.01)

(58) Field of Classification Search
None
See application file for complete search history.

(56) References Cited

U.S. PATENT DOCUMENTS

| | | | |
|---|---|---|---|
| 10,124,512 | B2 | 11/2018 | Boisart et al. |
| 10,287,561 | B2 | 5/2019 | Alvarez et al. |
| 10,385,183 | B2 | 8/2019 | Maille |
| 10,508,269 | B2 | 12/2019 | Li et al. |
| 10,584,320 | B2 | 3/2020 | Topham et al. |
| 10,590,401 | B2 | 3/2020 | Tournier et al. |
| 10,626,242 | B2 | 4/2020 | Ferreira et al. |
| 10,717,996 | B2 | 7/2020 | Dusseaux et al. |
| 10,723,848 | B2 | 7/2020 | Chateau et al. |
| 10,767,026 | B2 | 9/2020 | Desrousseaux et al. |
| 10,829,598 | B2 | 11/2020 | Ferreira et al. |
| 10,829,754 | B2 | 11/2020 | Marty et al. |
| 11,072,784 | B2 | 7/2021 | Tournier et al. |
| 11,198,767 | B2 | 12/2021 | Guemard et al. |
| 11,345,906 | B2 | 5/2022 | Marty et al. |
| 11,370,890 | B2 | 6/2022 | Ferreira et al. |
| 11,377,533 | B2 | 7/2022 | Desrousseaux et al. |
| 11,384,218 | B2 | 7/2022 | Guemard et al. |
| 11,414,651 | B2 | 8/2022 | Topham et al. |
| 11,535,832 | B2 | 12/2022 | David et al. |
| 2020/0339766 | A1 | 10/2020 | Chateau et al. |
| 2020/0385698 | A1 | 12/2020 | Marty et al. |
| 2021/0171921 | A1 | 6/2021 | Andre et al. |
| 2021/0180037 | A1 | 6/2021 | Duquesne et al. |
| 2021/0246400 | A1 | 8/2021 | Degering et al. |
| 2021/0254036 | A1 | 8/2021 | Degering et al. |
| 2022/0002516 | A1 | 1/2022 | Chateau |
| 2022/0177697 | A1 | 6/2022 | Guillamot et al. |
| 2022/0227957 | A1 | 7/2022 | Guemard et al. |
| 2022/0251327 | A1 | 8/2022 | Marty et al. |
| 2022/0282232 | A1 | 9/2022 | Tournier |
| 2022/0282235 | A1 | 9/2022 | Duquesne et al. |
| 2022/0363861 | A1 | 11/2022 | Marty |
| 2023/0034354 | A1 | 2/2023 | Chateau |
| 2023/0048275 | A1 | 2/2023 | Marty |
| 2023/0049607 | A1 | 2/2023 | Aloui Dalibey et al. |
| 2023/0392129 | A1 | 12/2023 | Tournier |
| 2023/0392130 | A1 | 12/2023 | Tournier |
| 2023/0399628 | A1 | 12/2023 | Tournier |

FOREIGN PATENT DOCUMENTS

| | | | |
|---|---|---|---|
| DE | 10 2018 210 608 | | 1/2020 |
| DE | 10 2018 210605 | * | 1/2020 |
| WO | WO 2013/033318 | | 3/2013 |
| WO | WO 2022/090288 | | 5/2022 |
| WO | WO 2022/090290 | | 5/2022 |
| WO | WO 2022/090293 | | 5/2022 |

OTHER PUBLICATIONS

Claims currently pending in U.S. Appl. No. 17/887,544, Aug. 19, 2022, pp. 1-3.
Claims as filed in U.S. Appl. No. 18/145,073, Dec. 22, 2022, pp. 1-4.
Written Opinion in International Application No. PCT/EP2021/079779, Apr. 4, 2022, pp. 1-15.
Wei, R. et al. "Functional characterization and structural modeling of synthetic polyester-degrading hydrolases from *Thermomonospora curvata" AMB Express*, 2014, pp. 1-10, vol. 4, No. 44.

(Continued)

*Primary Examiner* — Erin M. Bowers
(74) *Attorney, Agent, or Firm* — SALIWANCHIK, LLOYD & EISENSCHENK

(57) ABSTRACT

The present invention relates to novel esterases, more particularly to esterase variants having improved activity and/or improved thermostability compared to the esterase of SEQ ID NO: 1 and the uses thereof for degrading polyester containing material, such as plastic products. The esterases of the invention are particularly suited to degrade polyethylene terephthalate, and material containing polyethylene terephthalate.

25 Claims, No Drawings

Specification includes a Sequence Listing.

(56) References Cited

OTHER PUBLICATIONS

Schmidt, J. et al. "Degradation of Polyester Polyurethane by Bacterial Polyester Hydrolases" *Polymers*, Feb. 16, 2017, pp. 1-10, vol. 9, No. 65.
Samak, N. A. et al. "Recent advances in biocatalysts engineering for polyethylene terephthalate plastic waste green recycling" *Environment International*, available online Sep. 25, 2020, pp. 1-18, vol. 145, No. 106144.

* cited by examiner

ESTERASES AND USES THEREOF

CROSS-REFERENCE TO RELATED APPLICATION

This application is the U.S. national stage application of International Patent Application No. PCT/EP2021/079779, filed Oct. 27, 2021.

REFERENCE TO SEQUENCE LISTING

The Sequence Listing for this application is labeled "Seq-List.txt" which was created on Apr. 4, 2023, and is 2,472 bytes. The entire content of the sequence listing is incorporated herein by reference in its entirety.

The present invention relates to novel esterases, more particularly to esterases having improved activity and/or improved thermostability compared to a parent esterase. The present invention also relates to uses of said novel esterases for degrading polyester containing material, such as plastic products. The esterases of the invention are particularly suited to degrade polyethylene terephthalate, and polyethylene terephthalate containing material.

BACKGROUND

Esterases are able to catalyze the hydrolysis of a variety of polymers, including polyesters. In this context, esterases have shown promising effects in a number of industrial applications, including as detergents for dishwashing and laundry applications, as degrading enzymes for processing biomass and food, as biocatalysts in detoxification of environmental pollutants or for the treatment of polyester fabrics in the textile industry. The use of esterases as degrading enzymes for hydrolyzing polyethylene terephthalate (PET) is of particular interest. Indeed, PET is used in a large number of technical fields, such as in the manufacture of clothes, carpets, or in the form of a thermoset resin for the manufacture of packaging or automobile plastics, etc., so that PET accumulation in landfills becomes an increasing ecological problem.

The enzymatic degradation of polyesters, and particularly of PET, is considered as an interesting solution to decrease plastic waste accumulation. Indeed, enzymes may accelerate hydrolysis of polyester containing material, and more particularly of plastic products, even up to the monomer level. Furthermore, the hydrolysate (i.e., monomers and oligomers) can be recycled as material for synthesizing new polymers.

In this context, several esterases have been identified as candidate degrading enzymes for polyesters, and some variants of such esterases have been developed. Among esterases, cutinases, also known as cutin hydrolases (EC 3.1.1.74), are of particular interest. Cutinases have been identified from various fungi (P. E. Kolattukudy in "Lipases", Ed. B. Borg-strόm and H. L. Brockman, Elsevier 1984, 471-504), bacteria and plant pollen. Recently, metagenomics approaches have led to identification of additional esterases.

However, there is still a need for esterases with improved activity and/or improved thermostability compared to already known esterases, to provide polyester degrading processes more efficient and thereby more competitive.

SUMMARY OF THE INVENTION

The present invention provides new esterases exhibiting increased activity and/or increased thermostability compared to a parent, or wild-type esterase, having the amino acid sequence as set forth in SEQ ID No 1. This wild-type esterase corresponds to the amino acids 30 to 289 of the amino acid sequence of the esterase referenced under the accession number of D1A9G5 in Uniprot database (see World Wide Web: uniprot.org) and described as having a polyester degrading activity. The esterases of the present invention are particularly useful in processes for degrading plastic products, more particularly plastic products containing PET.

In this regard, it is an object of the invention to provide an esterase which (i) has at least 80%, 85%, 90%, 95%, 96%, 97%, 98% or 99% identity to the full length amino acid sequence set forth in SEQ ID No 1, and (ii) has at least one amino acid substitution at a position corresponding to residues selected from F209, T11, E12, T48, T63, S67, Q94, Y108, G135, P151, N156, D158, T168, F188, E197, E202, S207, F210, M218, K220, Q238, L240, P242, S251 and P258, and/or at least one amino acid substitution selected from A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C wherein the positions are numbered by reference to the amino acid sequence set forth in SEQ ID No 1, (iii) has a polyester degrading activity and preferably (iv) exhibits an increased thermostability and/or an increased degrading activity compared to the esterase of SEQ ID No 1.

Preferably, the esterase comprises at least one amino acid substitution at a position selected from T63, S67, Q94, G135, T168, F209 and S251, preferably selected from Q94, G135, T168, F209 and S251, more preferably at least one substitution at position F209, even more preferably selected from F209I/W and/or at least one amino acid substitution selected from S177H/Q/N/E, T183E, N204C/K/R, Q212D/M and S214P/D, preferably selected from T183E, N204C/K/R.

It is another object of the invention to provide a nucleic acid encoding an esterase of the invention. The present invention also relates to an expression cassette or an expression vector comprising said nucleic acid, and to a host cell comprising said nucleic acid, expression cassette or vector.

The present invention also provides a composition comprising an esterase of the present invention, a host cell of the present invention, or extract thereof.

It is a further object of the invention to provide a method of producing an esterase of the invention comprising:

(a) culturing the host cell according to the invention under conditions suitable to express a nucleic acid encoding an esterase; and optionally (b) recovering said esterase from the cell culture.

It is a further object of the invention to provide a method of degrading a polyester comprising (a) contacting the polyester with an esterase according to the invention or a host cell according to the invention or a composition according to the invention; and, optionally (b) recovering monomers and/or oligomers.

Particularly, the invention provides a method of degrading PET, comprising contacting PET with at least one esterase of the invention, and optionally recovering monomers and/or oligomers of PET.

The invention also relates to the use of an esterase of the invention for degrading PET or a plastic product containing PET.

The present invention also relates to a polyester containing material in which an esterase or a host cell or a composition of the invention is included.

The present invention also relates to a detergent composition comprising the esterase or host cell according to the invention or a composition comprising an esterase of the present invention.

DETAILED DESCRIPTION OF THE INVENTION

Definitions

The present disclosure will be best understood by reference to the following definitions.

Herein, the terms "peptide", "polypeptide", "protein", "enzyme" refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The term "esterase" refers to an enzyme which belongs to a class of hydrolases classified as EC 3.1.1 according to Enzyme Nomenclature that catalyzes the hydrolysis of esters into an acid and an alcohol. The term "cutinase" or "cutin hydrolase" refers to the esterases classified as EC 3.1.1.74 according to Enzyme Nomenclature that are able to catalyse the chemical reaction of production of cutin monomers from cutin and water.

The terms "wild-type protein" or "parent protein" refer to the non-mutated version of a polypeptide as it appears naturally. In the present case, the parent esterase refers to the esterase having the amino acid sequence as set forth in SEQ ID No 1.

The terms "mutant" and "variant" refer to polypeptides derived from SEQ ID No 1 and comprising at least one modification or alteration, i.e., a substitution, insertion, and/or deletion, at one or more (e.g., several) positions and having a polyester degrading activity. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Thus, the terms "modification" and "alteration" as used herein in relation to a particular position means that the amino acid in this particular position has been modified compared to the amino acid in this particular position in the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: L82A denotes that amino acid residue (Leucine, L) at position 82 of the parent sequence is substituted by an Alanine (A). A121V/I/M denotes that amino acid residue (Alanine, A) at position 121 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

Unless otherwise specified, the positions disclosed in the present application are numbered by reference to the amino acid sequence set forth in SEQ ID No 1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as World Wide Web: blast.ncbi.nlm.nih.gov/or ebi.ac.uk/Tools/emboss/. Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=11, Gap extend=1.

A "polymer" refers to a chemical compound or mixture of compounds whose structure is constituted of multiple monomers (repeat units) linked by covalent chemical bonds. Within the context of the invention, the term polymer includes natural or synthetic polymers, constituted of a single type of repeat unit (i.e., homopolymers) or of a mixture of different repeat units (i.e., copolymers or heteropolymers). According to the invention, "oligomers" refer to molecules containing from 2 to about 20 monomers.

In the context of the invention, a "polyester containing material" or "polyester containing product" refers to a product, such as plastic product, comprising at least one polyester in crystalline, semi-crystalline or totally amorphous forms. In a particular embodiment, the polyester containing material refers to any item made from at least one plastic material, such as plastic sheet, tube, rod, profile, shape, film, massive block, etc., which contains at least one polyester, and possibly other substances or additives, such as plasticizers, mineral or organic fillers. In another particular embodiment, the polyester containing material refers to a plastic compound, or plastic formulation, in a molten or solid state, suitable for making a plastic product. In another particular embodiment, the polyester containing material refers to textile, fabrics or fibers comprising at least one polyester. In another particular embodiment, the polyester containing material refers to plastic waste or fiber waste comprising at least one polyester.

In the present description, the term "polyester(s)" encompasses but is not limited to polyethylene terephthalate (PET), polytrimethylene terephthalate (PTT), polybutylene terephthalate (PBT), polyethylene isosorbide terephthalate (PEIT), polylactic acid (PLA), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA), polyethylene naphthalate (PEN) and blends/mixtures of these polymers.

New Esterases

The present invention provides novel esterases with improved activity and/or improved thermostability compared to a parent esterase. More particularly, the inventors have designed novel enzymes particularly suited for use in industrial processes. The esterases of the invention are particularly suited to degrade polyesters, more particularly PET, including PET containing material and particularly plastic product containing PET. In a particular embodiment, the esterases exhibit both an increased activity and an increased thermostability.

It is therefore an object of the present invention to provide esterases that exhibit an increased activity, compared to the esterase having the amino acid sequence as set forth in SEQ ID No 1, also referenced as parent esterase.

Particularly, the inventors have identified specific amino acid residues in SEQ ID No 1, which are intended to be in contact with a polymer substrate in the X-ray crystal structure (i.e., folded 3D structure) of the esterases that may be advantageously modified to promote the contact of the substrate with the esterases and advantageously leads to an increased adsorption of the polymer and/or thereby to an increased activity of the esterases on this polymer.

Within the context of the invention, the term "increased activity" or "increased degrading activity" indicates an increased ability of the esterase to degrade a polyester and/or an increased ability to adsorb on a polyester, at given conditions (e.g., temperature, pH, concentration) as compared to the ability of the esterase of SEQ ID No 1 to degrade and/or adsorb on same polyester at same conditions. Particularly, the esterase of the invention has an increased PET degrading activity. Such an increase may be at least 10% greater than the PET degrading activity of the esterase of SEQ ID No 1, preferably at least 20%, 30%, 40%, 50%, 60%, 70%, 80%, 90%, 100%, 110%, 120%, 130% or greater. Particularly, the degrading activity is a depolymerization activity leading to monomers and/or oligomers of the polyester, which can be further retrieved and optionally reused.

The "degrading activity" of an esterase may be evaluated by the one skilled in the art, according to methods known per se in the art. For instance, the degrading activity can be assessed by measurement of the specific polymer's depolymerization activity rate, the measurement of the rate to degrade a solid polymer compound dispersed in an agar plate, or the measurement of the polymer's depolymerization activity rate in reactor. Particularly, the degrading activity may be evaluated by measuring the "specific degrading activity" of an esterase. The "specific degrading activity" of an esterase for PET corresponds to μmol of PET hydrolyzed/min or mg of equivalent TA produced/hour and per mg of esterase during the initial period of the reaction (i.e. the first 24 hours) and is determined from the linear part of the hydrolysis curve of the reaction, such curve being set up by several samplings performed at different time during the first 24 hours. As another example, the "degrading activity" may be evaluated by measuring, after a defined period of time, the rate and/or yield of oligomers and/or monomers released under suitable conditions of temperature, pH and buffer, when contacting the polymer or the polymer-containing plastic product with a degrading enzyme.

The ability of an enzyme to adsorb on a substrate may be evaluated by the one skilled in the art, according to methods known per se in the art. For instance, the ability of an enzyme to adsorb on a substrate can be measured from a solution containing the enzyme and wherein the enzyme has been previously incubated with a substrate under suitable conditions.

The inventors have also identified target amino acid residues in SEQ ID No 1, that may be advantageously modified to improve the stability of corresponding esterases at high temperatures (i.e., improved thermostability), and advantageously at temperature above 50° C., preferably above 60° C., more preferably above 65° C.

It is therefore an object of the present invention to provide new esterases that exhibit increased thermostability as compared to the thermostability of the esterase having the amino acid sequence set forth in SEQ ID No 1 (i.e., the parent esterase).

Within the context of the invention, and unless otherwise specified, a given temperature corresponds to said temperature +/−1° C.

Within the context of the invention, the term "increased thermostability" indicates an increased ability of an esterase to resist to changes in its chemical and/or physical structure at high temperatures, and particularly at temperature between 50° C. and 90° C., as compared to the esterase of SEQ ID No 1. In a particular embodiment, the thermostability of the esterases is improved, as compared to the thermostability of the parent esterase, at temperature between 50° C. and 90° C., between 50° C. and 80° C., between 50° C. and 75° C., between 50° C. and 70° C., between 50° C. and 65° C., between 55° C. and 90° C., between 55° C. and 80° C., between 55° C. and 75° C., between 55° C. and 70° C., between 55° C. and 65° C., between 60° C. and 90° C., between 60° C. and 80° C., between 60° C. and 75° C., between 60° C. and 70° C., between 60° C. and 65° C., between 65° C. and 90° C., between 65° C. and 80° C., between 65° C. and 75° C., between 65° C. and 70° C. In a particular embodiment, the thermostability of the esterases is improved, as compared to the thermostability of the parent esterase, at least at 65° C.

Particularly, the thermostability may be evaluated through the assessment of the melting temperature (Tm) of the esterase. In the context of the present invention, the "melting temperature" refers to the temperature at which half of the enzyme population considered is unfolded or misfolded. Typically, esterases of the invention show an increased Tm of about 1° C., 2° C., 3° C., 4° C., 5° C., 10° C. or more, as compared to the Tm of the esterase of SEQ ID No 1. In particular, esterases of the present invention can have an increased half-life at a temperature between 50° C. and 90° C., as compared to the esterase of SEQ ID No 1. Particularly, esterases of the present invention can have an increased half-life at temperature between 50° C. and 90° C., between 50° C. and 80° C., between 50° C. and 75° C., between 50° C. and 70° C., between 50° C. and 65° C., between 55° C. and 90° C., between 55° C. and 80° C., between 55° C. and 75° C., between 55° C. and 70° C., between 55° C. and 65° C., between 60° C. and 90° C., between 60° C. and 80° C., between 60° C. and 75° C., between 60° C. and 70° C., between 60° C. and 65° C., between 65° C. and 90° C., between 65° C. and 80° C., between 65° C. and 75° C., between 65° C. and 70° C., as compared to the esterase of SEQ ID No 1. In a particular embodiment, the thermostability of the esterases is improved, as compared to the thermostability of the parent esterase, at least at 65° C.

The melting temperature (Tm) of an esterase may be measured by the one skilled in the art, according to methods known per se in the art. For instance, the DSF may be used to quantify the change in thermal denaturation temperature of the esterase and thereby to determine its Tm. Alternatively, the Tm can be assessed by analysis of the protein folding using circular dichroism. Preferably, the Tm is measured using DSF or circular dichroism as exposed in the experimental part. In the context of the invention, comparisons of Tm are performed with Tm that are measured under same conditions (e.g. pH, nature and amount of polyesters, etc.).

Alternatively, the thermostability may be evaluated by measuring the esterase activity and/or the polyester depolymerization activity of the esterase after incubation at different temperatures and comparing with the esterase activity and/or polyester depolymerization activity of the parent esterase. The ability to perform multiple rounds of polyester's depolymerization assays at different temperatures can also be evaluated. A rapid and valuable test may consist on the evaluation, by halo diameter measurement, of the esterase ability to degrade a solid polyester compound dispersed in an agar plate after incubation at different temperatures.

Thus, it is an object of the invention to provide an esterase which (i) has at least 80%, 85%, 90%, 95%, 96%, 97%, 98% or 99% identity to the full length amino acid sequence set forth in SEQ ID No 1, and (ii) has at least one amino acid substitution at a position selected from T11, E12, T48, T63, S67, Q94, Y108, G135, P151, N156, D158, T168, F188, E197, E202, S207, F209, F210, M218, K220, Q238, L240, P242, S251, P258, A23, T52, A55, F62, S65, S68, W71, L92, D96, R100, A121, A125, A127, E138, I152, L157, S177, P180, A182, T183, N204, N205, Q212, F213, S214, D216, T217, F221, P243, A246, 1247 and G248 wherein the positions are numbered by reference to the amino acid sequence set forth in SEQ ID No 1, and (iii) exhibits a polyester degrading activity and (iv) exhibits an increased thermostability and/or an increased degrading activity compared to the esterase of SEQ ID No 1.

It is an object of the invention to provide an esterase which (i) has at least 80%, 85%, 90%, 95%, 96%, 97%, 98% or 99% identity to the full length amino acid sequence set forth in SEQ ID No 1, and (ii) has at least one amino acid substitution at a position corresponding to residues selected from F209, T11, E12, T48, T63, S67, Q94, Y108, G135, P151, N156, D158, T168, F188, E197, E202, S207, F210, M218, K220, Q238, L240, P242, S251 and P258, and/or at least one amino acid substitution selected from A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C wherein the positions are numbered by reference to the amino acid sequence set forth in SEQ ID No 1, (iii) has a polyester degrading activity and preferably (iv) exhibits an increased thermostability and/or an increased degrading activity compared to the esterase of SEQ ID No 1.

Particularly, it is an object of the present invention to provide an esterase which (i) has at least 80%, 85%, 90%, 95%, 96%, 97%, 98% or 99% identity to the full length amino acid sequence set forth in SEQ ID No 1, and (ii) has at least one substitution at a position selected from the group consisting in T11, E12, T48, T63, S67, Q94, Y108, G135, P151, N156, D158, T168, F188, E197, E202, S207, F209, F210, M218, K220, Q238, L240, P242, S251 and P258 wherein the positions are numbered by reference to the amino acid sequence set forth in SEQ ID No 1, (iii) has a polyester degrading activity and preferably (iv) exhibits an increased thermostability and/or an increased degrading activity compared to the esterase of SEQ ID No 1. Particularly, the substitution is selected from T11N/D/E/I/M/Q/S, E12F/H/Y/R//D/E/G/L/N/P/QN, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C and P258S, more preferably selected from T11N, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C and P258S.

In a particular embodiment, the esterase comprises at least one amino acid substitution at position selected from T63, S67, Q94, G135, T168, F209 and S251 preferably at least one substitution selected from T63M/V, S67T, Q94G/P/N/Q/T/Y, G135A, T168Q/V, F209I/W/A/G/H/L/N/R/S/T/M and S251C, more preferably selected from T63M, S67T, Q94G/P, G135A, T168Q, F209I/W and S251C.

In a preferred embodiment, the esterase comprises at least one amino acid substitution at a position selected from Q94, G135, T168, F209 and S251 preferably at least one substitution selected from Q94G/P/N/Q/T/Y, G135A, T168Q/V, F209I/W/A/G/H/L/N/R/S/T/M and S251C, more preferably selected from Q94G/P, G135A, T168Q, F209I/W and S251C.

In an embodiment, the esterase comprises at least one substitution at position F209, preferably at least one substitution selected from F209I/W/A/G/H/L/N/R/S/T/M, more preferably selected from F209I/W, even more preferably the substitution F209I.

In an embodiment, the esterase comprises at least one substitution at position S251, preferably at least the substitution S251C.

In an embodiment, the esterase further comprises at least one substitution at position selected from A23, T52, A55, F62, S65, S68, W71, L92, D96, R100, A121, A125, A127, E138, 1152, L157, S177, P180, A182, T183, N204, N205, Q212, F213, S214, D216, T217, P243, A246, 1247 and G248, preferably selected from A23P, T52P/E, A55L, F62M, S65N/Q, S68H, W71R/D/E/M, L92W/F, D96S, R100S/Q, A121R/W, A125G, A127G, E138R, I152Q, L157E/G/N/Q/W/T, S177H/Q/N/E, P180E/D, A182R, T183E/D, N204C/K/R, N205K/G, Q212D/M/E/H/Y, F213D/M, S214P/D, D216P/N, T217A, P243V/Y, A246Y/C/E/D, I247Y/T and G248C.

In a preferred embodiment, the esterase further comprises at least one substitution at a position selected from T183, N204 and S214, preferably selected from T183E/D, N204C/K/R and S214P/D, even more preferably selected from T183E, N204C/K/R and S214P.

In a particular embodiment, the esterase has the amino acid sequence set forth in SEQ ID No 1 with one to twenty-five amino acid substitutions, as compared to SEQ ID No 1, at position(s) selected from T11, E12, T48, T63, S67, Q94, Y108, G135, P151, N156, D158, T168, F188, E197, E202, S207, F209, F210, M218, K220, Q238, L240, P242, S251 and P258, preferably selected from T11N/D/E/I/M/Q/S, E12F/H/Y/R//D/E/G/L/N/P/QN, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C and P258S, more preferably one to twenty-five amino acid substitutions selected from TI IN, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C and P258S.

Preferably, the esterase has the amino acid sequence set forth in SEQ ID No 1 with one to seven substitutions, as compared to SEQ ID No 1, at position(s) selected from the group consisting in T63, S67, Q94, G135, T168, F209 and S251 preferably one to seven substitutions selected from T63M/V, S67T, Q94G/P/N/Q/T/Y, G135A, T168Q/V, F209I/W/A/G/H/L/N/R/S/T/M and S251C, more preferably selected from T63M, S67T, Q94G/P, G135A, T168Q, F209I/W and S251C. More preferably, the esterase has one to five substitutions at position(s) selected from the group consisting in Q94, G135, T168, F209 and S251C, preferably one to five substitutions selected from Q94G/P/N/Q/T/Y, G135A, T168Q/V, F209I/W/A/G/H/L/N/R/S/T/M and S251C, more preferably selected from Q94G/P, G135A, T168Q, F209I/W and S251C.

In a particular embodiment, the esterase has the amino acid sequence set forth in SEQ ID No 1 with a single amino acid substitution, as compared to SEQ ID No 1, at a position selected from T11, E12, T48, T63, S67, Q94, Y108, G135, P151, N156, D158, T168, F188, E197, E202, S207, F209, F210, M218, K220, Q238, L240, P242, S251 and P258, preferably a single substitution selected from T11N/D/E/I/M/Q/S, E12F/H/Y/R//D/E/G/L/N/P/Q/V, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C and P258S, more preferably selected from TI IN, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C and P258S.

Preferably, the esterase has the amino acid sequence set forth in SEQ ID No 1 with a single amino acid substitution, as compared to SEQ ID No 1, at a position selected from the group consisting in T63, S67, Q94, G135, T168, F209 and S251, preferably a single substitution selected from T63M/V, S67T, Q94G/P/N/Q/T/Y, G135A, T168Q/V, F209I/W/A/G/H/L/N/R/S/T/M and S251C, more preferably selected from T63M, S67T, Q94G/P, G135A, T168Q, F209I/W and S251C. More preferably, the esterase has a single substitution, as compared to SEQ ID No 1, at a position selected from the group consisting in Q94, G135, T168 and F209, preferably a single substitution selected from Q94G/P/N/Q/T/Y, G135A, T168Q/V, F209I/W/A/G/H/L/N/R/S/T/M, more preferably selected from Q94G/P, G135A, T168Q and F209I/W.

It is also an object of the invention to provide an esterase which (i) has at least 80%, 85%, 90%, 95%, 96%, 97%, 98% or 99% identity to the full length amino acid set forth in SEQ ID No 1, (ii) has at least one substitution selected from the group consisting in A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, and (iii) has a polyester degrading activity and preferably (iv) exhibits an increased thermostability and/or an increased degrading activity compared to the esterase of SEQ ID No 1.

Particularly, the esterase has at least one substitution selected from the group consisting in A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204C/K/R, N205K, Q212D/M, F213D/M, S214P/D, D216P, T217A, P243V/Y, A246Y/C/E, I247Y/T and G248C.

In an embodiment, the esterase comprises at least one amino acid substitution selected from N204K/R and at least the amino acid residue S251 as in the parent esterase.

In an embodiment, the esterase comprises at least one amino acid substitution selected from S177H/Q/N/E, T183E, N204C/K/R, Q212D/M and S214P/D, preferably selected from S177H/Q/N, T183E, N204C, Q212D/M and S214P/D. Preferably, the esterase comprises at least one amino acid substitution selected from T183E, N204C/K/R and S214P/D, more preferably selected from T183E, N204C and S214P/D.

In another embodiment, the esterase further comprises at least one amino acid substitution at position selected from T11, E12, T48, T63, S67, Q94, Y108, G135, P151, N156, D158, T168, F188, E197, E202, S207, F209, F210, M218, K220, Q238, L240, P242, S251 and P258, preferably at least one amino acid substitution selected from T11N/D/E/I/M/Q/S, E12F/H/Y/R//D/E/G/L/N/P/Q/V, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C and P258S, more preferably selected from TI IN, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C and P258S, even more preferably selected from Q94G/P, G135A, T168Q, F209I/W and S251C. In a particular embodiment, the esterase has the amino acid sequence set forth in SEQ ID No 1 with a one to thirty-one amino acid substitutions, as compared to SEQ ID No 1, selected from the group consisting in A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, preferably selected from A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204C/K/R, N205K, Q212D/M, F213D/M, S214P/D, D216P, T217A, P243V/Y, A246Y/C/E, I247Y/T and G248C. Particularly, the esterase has the amino acid sequence set forth in SEQ ID No 1 with one to five amino acid substitutions, as compared to SEQ ID No 1, selected from the group consisting in S177H/Q/N/E, T183E, N204C/K/R, Q212D/M and S214P/D, preferably selected from S177H/Q/N, T183E, N204K/R, Q212D/M and S214P/D, more preferably with one to three substitutions selected from T183E, N204K/R and S214P/D.

In a particular embodiment, the esterase has the amino acid sequence set forth in SEQ ID No 1 with a single amino acid substitution selected from the group consisting in A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, preferably selected from A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204C/K/R, N205K, Q212D/M, F213D/M, S214P/D, D216P, T217A, P243V/Y, A246Y/C/E, I247Y/T and G248C. Particularly, the esterase has the amino acid sequence set forth in SEQ ID No 1 with a single amino acid substitution, as compared to SEQ ID No 1, selected from the group consisting in S177H/Q/N/E, T183E, N204C/K/R, Q212D/M and S214P/D, preferably selected from S177H/Q/N, T183E, N204K/R, Q212D/M and S214P/D, more preferably selected from T183E, N204K/R and S214P/D.

It is also an object of the invention to provide an esterase which comprises at least one amino acid substitution at a position selected from T63, S67, Q94, G135, T168, F209 and S251, preferably selected from Q94, G135, T168, F209 and S251, and/or at least one amino acid substitution selected from S177H/Q/N/E, T183E, N204C/K/R, Q212D/M and S214P/D, preferably selected from T183E, N204C/K/R and S214P/D.

Particularly, the esterase comprises at least one amino acid substitution selected from T11N/D/E/I/M/Q/S, E12F/H/Y/R//D/E/G/L/N/P/Q/V, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C, P258S, A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, preferably selected from TI IN, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C, P258S, A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204C/K/R, N205K, Q212D/M, F213D/M, S214P/D, D216P, T217A, P243V/Y, A246Y/C/E, I247Y/T and G248C. Particularly, the esterase comprises at least one amino acid substitution selected from T63M/V, S67T, Q94G/P/N/Q/T/Y, G135A, T168Q/V, F209I/W/A/G/H/L/N/R/S/T/M, S251C, S177H/Q/N/E, T183E, N204C/K/R, Q212D/M and S214P/D, preferably selected from T63M, S67T, Q94G/P, G135A, T168Q, F209I/W, S251C, S177N, T183E, N204C, Q212D/M and S214P.

In a preferred embodiment, the esterase comprises at least one amino acid substitution selected from Q94G/P/N/Q/T/Y, G135A, T168Q/V, F209I/W/A/G/H/L/N/R/S/T/M, S251C, T183E, N204C/K/R, and S214P/D, preferably selected from Q94G/P, G135A, T168Q, F209I/W, S251C, T183E, N204C and S214P, more preferably selected from Q94G, G135A, T168Q, F209I, S251C, T183E, N204C and S214P.

In an embodiment, the esterase comprises at least one amino acid substitution selected from N204K/R and at least the amino acid residue S251 as in the parent esterase.

In a particular embodiment, the esterase has at least 80%, 85%, 90%, 95%, 96%, 97%, 98% or 99% identity to the full length amino acid sequence set forth in SEQ ID No 1 and has at least substitutions at the combination of positions N204+S251, preferably a combination of substitutions selected from N204C/K/R+S251C, more preferably the combination N204C+S251C. In a particular embodiment, the esterase has the amino acid sequence set forth in SEQ ID No 1 with the combination of substitutions N204C/K/R+S251C, preferably selected from N204C+S251C. In an embodiment, the esterase has an amino acid sequence that consists of the amino acid sequence set forth in SEQ ID No 1 with the combination of substitutions selected from N204C/K/R+S251C, preferably N204C+S251C.

In another embodiment, the esterase comprises a combination of substitutions selected from N204C/K/R+S251C, preferably the combination of substitutions N204C+S251C, and at least one additional amino acid substitution, preferably at least two additional substitutions, more preferably at least three additional substitutions, at positions selected from T63, S67, Q94, G135, T168, S177, T183, F209, Q212 and S214, preferably at positions selected from Q94, G135, T168, T183, F209 and S214. Preferably, the esterase comprises the combination of substitutions N204C/K/R+S251C, preferably the combination of substitutions N204C+S251C, and at least one additional amino acid substitution, preferably at least two, more preferably at least three additional substitutions, selected from T63M/V, S67T, Q94G/P/N/T/Y, G135A, T168Q/V, S177H/Q/N, T183E, F209I/W/A/G/H/L/N/R/S/T/M, Q212D/M and S214P/D, preferably selected from Q94G/P/N/T/Y, G135A, T168Q/V, T183E, F209I/W/A/G/H/L/N/R/S/T/M and S214P/D. More preferably, the combination of substitutions is N204C+S251C and the additional amino acid substitutions are selected from T63M, S67T, Q94G/P, G135A, T168Q, S177N, T183E, F209I/W, Q212D/M and S214P, preferably selected from Q94G/P, G135A, T168Q, T183E, F209I/W and S214P, more preferably selected from Q94G, G135A, T168Q, T183E, F209I/W and S214P.

In a preferred embodiment, the esterase comprises a combination of substitutions at positions F209+S251+N204, preferably a combination of substitutions selected from F209I/W/A/G/H/L/N/R/S/T/M+S251C+N204C/K/R, more preferably the combination of substitutions F209I/W+S251C+N204C.

Particularly, the esterase comprises the combination of substitutions at positions F209+S251+N204 and at least one additional substitution, preferably at least two additional substitutions at positions selected from T63, S67, Q94, G135, T168, S177, T183, Q212 and S214, preferably at positions selected from Q94, G135, T168, T183 and S214. Preferably, the esterase comprises the combination of substitutions selected from F209I/W/A/G/H/L/N/R/S/T/M+S251C+N204C/K/R and at least one additional amino acid substitution, preferably at least two additional substitutions selected from T63M/V, S67T, Q94G/P/N/T/Y, G135A, T168Q/V, S177H/Q/N, T183E, Q212D/M and S214P/D, preferably selected from Q94G/P/N/T/Y, G135A, T168Q/V, T183E, and S214P/D. More preferably, the combination of substitutions selected from F209I/W+S251C+N204C and the additional amino acid substitutions are selected from T63M, S67T, Q94G/P, G135A, T168Q, S177N, T183E, Q212D/M and S214P, preferably selected from Q94G/P, G135A, T168Q, T183E and S214P, more preferably selected from Q94G, G135A, T168Q, T183E and S214P.

In an embodiment, the esterase comprises at least substitutions at the combination of positions F209+N204+S251+Q94, preferably selected from F209I/W/A/G/H/L/N/R/S/T/M+N204C+S251C+Q94G/P, more preferably selected from F209I/W+N204C+S251C+Q94G, even more preferably F209I+N204C+S251C+Q94G.

In another particular embodiment, the esterase comprises at least one combination of substitutions selected from N204C/K/R+S251C, F209I/W/A/G/H/L/N/R/S/T/M+N204C/K/R+S251C, F209I/W/A/G/H/L/N/R/S/T/M+N204C/K/R+S251C+Q94G/P, F209I/W/A/G/H/L/N/R/S/T/M+N204C/K/R+S251C+Q212D/M, F209I/W/A/G/H/L/N/R/S/T/M+N204C/K/R+S251C+Q94G/P+S214P/D+G135A+T168Q, F209I/W/A/G/H/L/N/R/S/T/M+N204C/K/R+S251C+Q94G/P+S214P/D+G135A+T168Q+T183E, F209I/W/A/G/H/L/N/R/S/T/M+N204C/K/R+S251C+Q94G/P+S214P/D+T183E and F209I/W/A/G/H/L/N/R/S/T/M+N204C/K/R+S251C+Q94G/P+S214P/D+T183E+T168Q preferably selected from N204C+S251C, F209I/W+N204C+S251C, F209I/W+N204C+S251C+Q94G, F209I/W+N204C+S251C+Q212M, F209I/W+N204C+S251C+Q94G+S214P+G135A+T168Q, F209I/W+N204C+S251C+Q94G+S214P+G135A+T168Q+T183E, F209I/W+N204C+S251C+Q94G+S214P+T183E and F209I/W+N204C+S251C+Q94G+S214P+T183E+T168Q, more preferably selected from N204C+S251C, F209I+N204C+S251C+Q94G, F209I+N204C+S251C+Q94G+S214P+T183E and F209I+N204C+S251C+Q94G+S214P+G135A+T168Q+T183E. Advantageously, this esterase exhibits both an increased thermostability and an increased polyester degrading activity compared to the esterase of SEQ ID No 1. In a particular embodiment, this esterase exhibits both an increased thermostability and an increased polyester degrading activity compared to the esterase of SEQ ID No 1 at 65° C.

In an embodiment, the esterase further comprises at least one substitution at positions selected from L14, A64, R75, E87, T88, A179, A206, N215, A219, F239, R245, D249, 1250, R100, L157, I178, N205 and F221. Preferably the esterase further comprises at least one substitution selected from L14D/E, A64D/S, R75C/D/E/F/G/I/M/N/Q/SN, E87A/E/F, T88E/S, A179C, A206D, N215C/D/E, A219E, F239E, R245C/E, D249E/H/S, 1250T, R100Q, L157T, I178V, N205G and F221Y.

In an embodiment, the esterase has the amino acid sequence set forth in SEQ ID No 1 with one to fifty-six amino acid substitutions, as compared to SEQ ID No 1, selected from T11N/D/E/I/M/Q/S, E12F/H/Y/R//D/E/G/L/N/P/Q/V, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C, P258S, A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, preferably selected from T11N, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C, P258S, A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204K/R, N205K, Q212D/M, F213D/M, S214P/D, D216P, T217A, P243V/Y, A246Y/C/E, I247Y/T and G248C. Preferably the esterase has the amino acid sequence set forth in SEQ ID No 1 with one to ten amino acid substitutions selected from Q94G/P/N/Q/T/Y, G135A, T168Q/V, F209I/W/A/G/H/L/N/R/S/T/M, S251C, S177H/Q/N/E, T183E, N204C/K/R, Q212D/M and S214P/D, more preferably with one to eight substitutions selected from Q94G/P/N/Q/T/Y, G135A, T168Q/V, F209I/W/A/G/H/L/N/R/S/T/M, S251C, T183E, N204C/K/R and S214P/D, even more preferably selected from Q94G, G135A, T168Q, F209I, S251C, T183E, N204C and S214P.

In an embodiment, the esterase has the amino acid sequence set forth in SEQ ID No 1 with a single amino acid substitution, as compared to SEQ ID No 1, selected from T11N/D/E/I/M/Q/S, E12F/H/Y/R//D/E/G/L/N/P/Q/V, T48A, T63M/V, S67T, Q94G/P/N/Q/T/Y, Y108Q, G135A, P151A, N156H, D158Q, T168Q/V, F188I/Y, E197P, E202M, S207D/L, F209I/W/A/G/H/L/N/R/S/T/M, F210T/A, M218I, K220E, Q238D/T, L240A, P242K, S251C, P258S, A23P, T52P/E, A55L, F62M, S65N/Q, S68H, W71R/D/E/M, L92W/F, D96S, R100S, A121R/W, A125G, A127G, E138R, I152Q, L157E/G/N/Q/W, S177H/Q/N/E, P180E/D, A182R, T183E/D, N204C/K/R, N205K, Q212D/M/E/H/Y, F213D/M, S214P/D, D216P/N, T217A, P243V/Y, A246Y/C/E/D, I247Y/T and G248C, preferably selected from T11N, E12F/H/Y/R, T48A, T63M, S67T, Q94G/P, Y108Q, G135A, P151A, N156H, D158Q, T168Q, F188I, E197P, E202M, S207D/L, F209I/W, F210T/A, M218I, K220E, Q238D, L240A, P242K, S251C, P258S, A23P, T52P/E, A55L, F62M, S65N/Q, S68H, W71R, L92W/F, D96S, R100S, A121R/W, A125G, A127G, E138R, I152Q, L157E/G/N/Q/W, S177H/Q/N, P180E, A182R, T183E, N204K/R, N205K, Q212D/M, F213D/M, S214P/D, D216P, T217A, P243V/Y, A246Y/C/E, I247Y/T and G248C. Preferably the single substitution is selected from Q94G/P/N/Q/T/Y, G135A, T168Q/V, F209I/W/A/G/H/L/N/R/S/T/M, S251C, S177H/Q/N/E, T183E, N204K/R, Q212D/M and S214P/D, more preferably selected from Q94G/P/N/Q/T/Y, G135A, T168Q/V, F209I/W/A/G/H/L/N/R/S/T/M, S251C, T183E, N204K/R and S214P/D, even more preferably selected from Q94G, G135A, T168Q, F209I, T183E and S214P.

In a particular embodiment, the amino acid sequence of the esterase consists in the amino acid sequence as set forth in SEQ ID No 1 with a single combination of substitutions, as compared to SEQ ID No 1, selected from N204C+S251C, F209I/W/A/G/H/L/N/R/S/T/M+N204C+S251C, F209I/W/A/G/H/L/N/R/S/T/M+N204C+S251C+Q94G/P, F209I/W/A/G/H/L/N/R/S/T/M+N204C+S251C+Q212D/M, F209I/W/A/G/H/L/N/R/S/T/M+N204C+S251C+Q94G/P+S214P/D+G135A+T168Q, F209I/W/A/G/H/L/N/R/S/T/M+N204C+S251C+Q94G/P+S214P/D+G135A+T168Q+T183E, F209I/W/A/G/H/L/N/R/S/T/M+N204C+S251C+Q94G/P+S214P/D+T183E and F209I/W/A/G/H/L/N/R/S/T/M+N204C+S251C+Q94G/P+S214P/D+T183E+T168Q preferably selected from N204C+S251C, F209I/W+N204C+S251C, F209I/W+N204C+S251C+Q94G, F209I/W+N204C+S251C+Q212M, F209I/W+N204C+S251C+Q94G+S214P+G135A+T168Q, F209I/W+N204C+S251C+Q94G+S214P+G135A+T168Q+T183E, F209I/W+N204C+S251C+Q94G+S214P+T183E and F209I/W+N204C+S251C+Q94G+S214P+T183E+T168Q, more preferably selected from N204C+S251C, F209I+N204C+S251C+

Q94G, F209I+N204C+S251C+Q94G+S214P+T183E and F209I+N204C+S251C+Q94G+S214P+G135A+T168Q+T183E. Advantageously, this esterase exhibits both an increased thermostability and an increased polyester degrading activity compared to the esterase of SEQ ID No 1. In a particular embodiment, this esterase exhibits both an increased thermostability and an increased polyester degrading activity compared to the esterase of SEQ ID No 1 at least at 65° C.

In an embodiment, the esterase comprises at least one amino acid residue selected from C241, C257, E174, S130, D176, H208, G61, F62, M131, A70, T136, H129, G132, W155, I171, I178, R91, T217 and S65 as in the parent esterase, i.e. the esterase of the invention is not modified at one, two, three, etc., or all of these positions.

In an embodiment, the esterase comprises at least the amino acids S130, D176 and H208 forming the catalytic site of the esterase and/or the amino acids C241 and C257 forming disulphide bond as in the parent esterase. Preferably, the esterase comprises a least one combination selected from C241+C257, S130+D176+H208 and C241+C257+S130+D176+H208 as in the parent esterase. In an embodiment, the esterase comprises the combination C241+C257+S130+D176+H208+E174+M131 as in the parent esterase.

In an embodiment, the esterase comprises at least one amino acid selected from A70, T136, H129, G132, W155, I171, I178, R91, T217 and S65 as in the parent esterase. Preferably, the esterase comprises at least one amino acid selected from I171 and I178 as in the parent esterase, more preferably at least the combination I171+I178 as in the parent esterase. In an embodiment, the esterase comprises the combination I171+I178+A70+T136+H129+G132+W155+R91+T217+S65 as in the parent esterase.

Preferably, the esterase comprises the combination C241+C257+S130+D176+H208+I171+I178 as in the parent esterase.

Polyester Degrading Activity of the Variant

It is an object of the invention to provide new enzymes having an esterase activity. In a particular embodiment, the enzyme of the invention exhibits a cutinase activity.

In a particular embodiment, the esterase of the invention has a polyester degrading activity, preferably a polyethylene terephthalate (PET) degrading activity, and/or a polybutylene adipate terephthalate (PBAT) degrading activity and/or a polycaprolactone (PCL) degrading activity and/or a polybutylene succinate (PBS) activity, more preferably a polyethylene terephthalate (PET) degrading activity, and/or a polybutylene adipate terephthalate (PBAT) degrading activity. Even more preferably, the esterase of the invention has a polyethylene terephthalate (PET) degrading activity.

Advantageously, the esterase of the invention exhibits a polyester degrading activity at least in a range of temperatures from 20° C. to 90° C., preferably from 30° C. to 90° C., more preferably from 40° C. to 90° C., more preferably from 50° C. to 90° C., even more preferably from 60° C. and 90° C. Particularly, the esterase of the invention exhibits a polyester degrading activity in a range of temperatures from 35° C. and 90° C., and 85° C., 35° C. and 80° C., 35° C. and 75° C., 35° C. and 70° C., 35° C. and 65° C., 35° C. and 60° C., 35° C. and 55° C., 35° C. and 50° C. In a particular embodiment, the esterase exhibits a polyester degrading activity at least at 60° C. In a particular embodiment, the esterase exhibits a polyester degrading activity at least at 65° C. In a particular embodiment, the esterase exhibits a polyester degrading activity at least at 70° C. In a particular embodiment, a polyester degrading activity is still measurable at a temperature between 55° C. and 70° C. As exposed above, the temperatures must be considered +/−1° C.

In a particular embodiment, the esterase of the invention has an increased polyester degrading activity at a given temperature, compared to the esterase of SEQ ID No 1, and more particularly at a temperature between 40° C. and 90° C., more preferably between 50° C. and 90° C.

In a particular embodiment, the esterase has a polyester degrading activity at 65° C. at least 5% higher than the polyester degrading activity of the esterase of SEQ ID No 1, preferably at least 10%, 20%, 50%, 100% or more.

In a particular embodiment, the esterase of the invention exhibits a measurable esterase activity at least in a range of pH from 5 to 9, preferably in a range of pH from 6 to 9, more preferably in a range of pH from 6.5 to 9, even more preferably in a range of pH from 6.5 to 8.

Nucleic Acids, Expression Cassette, Vector, Host Cell

It is a further object of the invention to provide a nucleic acid encoding an esterase as defined above.

As used herein, the term “nucleic acid”, “nucleic sequence,” “polynucleotide”, “oligonucleotide” and “nucleotide sequence” refer to a sequence of deoxyribonucleotides and/or ribonucleotides. The nucleic acids can be DNA (cDNA or gDNA), RNA, or a mixture thereof. It can be in single stranded form or in duplex form or a mixture thereof. It can be of recombinant, artificial and/or synthetic origin and it can comprise modified nucleotides, comprising for example a modified bond, a modified purine or pyrimidine base, or a modified sugar. The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding an esterase as defined above. Preferably, such stringent conditions include incubations of hybridization filters at about 42° C. for about 2.5 hours in 2× SSC/0.1% SDS, followed by washing of the filters four times of 15 minutes in 1× SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding an esterase of the invention, wherein the sequence of said nucleic acids, or a portion of said sequence at least, has been engineered using optimized codon usage.

Alternatively, the nucleic acids according to the invention may be deduced from the sequence of the esterase according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell.

The term "expression", as used herein, refers to any step involved in the production of a polypeptide including, but being not limited to, transcription, post-transcriptional modification, translation, post-translational modification, and secretion.

The term "expression cassette" denotes a nucleic acid construct comprising a coding region, i.e. a nucleic acid of the invention, and a regulatory region, i.e. comprising one or more control sequences, operably linked.

Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding an esterase of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the esterase. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

As used herein, the terms "vector" or "expression vector" refer to a DNA or RNA molecule that comprises an expression cassette of the invention, used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced. Preferably, the expression vector is a linear or circular double stranded DNA molecule.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be an eukaryotic cell, such as a yeast, fungal, mammalian, insect or plant cell. In a particular embodiment, the host cell is selected from the group of *Escherichia coli, Bacillus, Streptomyces, Trichoderma, Aspergillus, Saccharomyces, Pichia, Vibrio* or *Yarrowia.*

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation.

Optionally, more than one copy of a nucleic acid, cassette or vector of the present invention may be inserted into a host cell to increase production of the variant.

In a particular embodiment, the host cell is a recombinant microorganism. The invention indeed allows the engineering of microorganisms with improved capacity to degrade polyester containing material. For instance, the sequence of the invention may be used to complement a wild type strain of a fungus or bacterium already known as able to degrade polyester, in order to improve and/or increase the strain capacity.

Production of Esterase

It is another object of the invention to provide a method of producing an esterase of the invention, comprising expressing a nucleic acid encoding the esterase and optionally recovering the esterase.

In particular, the present invention relates to in vitro methods of producing an esterase of the present invention comprising (a) contacting a nucleic acid, cassette or vector of the invention with an in vitro expression system; and (b) recovering the esterase produced. In vitro expression systems are well-known by the person skilled in the art and are commercially available.

Preferably, the method of production comprises (a) culturing a host cell that comprises a nucleic acid encoding an esterase of the invention under conditions suitable to express the nucleic acid; and optionally (b) recovering said esterase from the cell culture.

Advantageously, the host cell is a recombinant *Bacillus*, recombinant *E. coli*, recombinant *Aspergillus*, recombinant *Trichoderma*, recombinant *Streptomyces*, recombinant *Saccharomyces*, recombinant *Pichia*, recombinant *Vibrio* or recombinant *Yarrowia*.

The host cells are cultivated in a nutrient medium suitable for production of polypeptides, using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the enzyme to be expressed and/or isolated. The cultivation takes place in a suitable nutrient medium, from commercial suppliers or prepared according to published compositions (e.g., in catalogues of the American Type Culture Collection).

If the esterase is excreted into the nutrient medium, the esterase can be recovered directly from the culture supernatant. Conversely, the esterase can be recovered from cell lysates or after permeabilisation. The esterase may be recovered using any method known in the art. For example, the esterase may be recovered from the nutrient medium by conventional procedures including, but not limited to, collection, centrifugation, filtration, extraction, spray-drying, evaporation, or precipitation. Optionally, the esterase may be partially or totally purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides.

The esterase may be used as such, in purified form, either alone or in combinations with additional enzymes, to catalyze enzymatic reactions involved in the degradation and/or recycling of polyester(s) and/or polyester containing material, such as plastic products containing polyester. The esterase may be in soluble form, or on solid phase. In particular, it may be bound to cell membranes or lipid vesicles, or to synthetic supports such as glass, plastic, polymers, filter, membranes, e.g., in the form of beads, columns, plates and the like.

Composition

It is a further object of the invention to provide a composition comprising an esterase, or a host cell of the invention, or extract thereof containing the esterase. In the context of the invention, the term "composition" encompasses any kind of compositions comprising an esterase or host cell of the invention, or an extract thereof containing the esterase.

The composition of the invention may comprise from 0.1% to 99.9%, preferably from 0.1% to 50%, more preferably from 0.1% to 30%, even more preferably from 0.1% to 5% by weight of esterase, based on the total weight of the composition. Alternatively, the composition may comprise between 5 and 10% by weight of esterase of the invention.

The composition may be in liquid or dry form, for instance in the form of a powder. In some embodiments, the composition is a lyophilisate.

The composition may further comprise excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polypropylene glycol, propylene glycol, sequestering agent such as EDTA, reducing agents, amino acids, a carrier such as a solvent or an aqueous solution, and the like. The composition of the invention may be obtained by mixing the esterase with one or several excipients.

In a particular embodiment, the composition comprises from 0.1% to 99.9%, preferably from 50% to 99.9%, more preferably from 70% to 99.9%, even more preferably from 95% to 99.9% by weight of excipient(s), based on the total weight of the composition. Alternatively, the composition may comprise from 90% to 95% by weight of excipient(s).

In a particular embodiment, the composition may further comprise additional polypeptide(s) exhibiting an enzymatic activity. The amounts of esterase of the invention will be easily adapted by those skilled in the art depending e.g., on the nature of the polyester to degrade and/or the additional enzymes/polypeptides contained in the composition.

In a particular embodiment, the esterase of the invention is solubilized in an aqueous medium together with one or several excipients, especially excipients which are able to stabilize or protect the polypeptide from degradation. For instance, the esterase of the invention may be solubilized in water, eventually with additional components, such as glycerol, sorbitol, dextrin, starch, glycol such as propanediol, salt, etc. The resulting mixture may then be dried so as to obtain a powder. Methods for drying such mixture are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a particular embodiment, the composition is under powder form and comprises esterase and a stabilizing/solubilizing amount of glycerol, sorbitol or dextrin, such as maltodextrine and/or cyclodextrine, starch, glycol such as propanediol, and/or salt.

In a particular embodiment, the composition of the invention comprises at least one recombinant cell expressing an esterase of the invention, or an extract thereof. An "extract of a cell" designates any fraction obtained from a cell, such as cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several recombinant cells of the invention or extract thereof, and optionally one or several additional cells.

In an embodiment, the composition consists or comprises a culture medium of a recombinant microorganism expressing and excreting an esterase of the invention. In a particular embodiment, the composition comprises such culture medium lyophilized.

Uses of Esterase

It is a further object of the invention to provide methods using an esterase of the invention for degrading and/or recycling in aerobic or anaerobic conditions polyester, or polyester containing material. The esterases of the invention are particularly useful for degrading PET and PET containing material.

It is therefore an object of the invention to use an esterase of the invention, or corresponding recombinant cell or extract thereof, or composition for the enzymatic degradation of a polyester.

In a particular embodiment, the polyester targeted by the esterase is selected from polyethylene terephthalate (PET), polytrimethylene terephthalate (PTT), polybutylene terephthalate (PBT), polyethylene isosorbide terephthalate (PEIT), polylactic acid (PLA), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly (ethylene adipate) (PEA), polyethylene naphthalate (PEN) and blends/mixtures of these materials, preferably polyethylene terephthalate.

In a preferred embodiment, the polyester is PET, and at least monomers (e.g., monoethylene glycol or terephthalic acid), and/or oligomers (e.g., methyl-2-hydroxyethyl terephthalate (MHET), bis(2-hydroxyethyl) terephthalate (BHET), 1-(2-Hydroxyethyl) 4-methyl terephthalate (HEMT) and dimethyl terephthalate (DMT)) are recovered.

It is also an object of the invention to use an esterase of the invention, or corresponding recombinant cell or extract thereof, or composition for the enzymatic degradation of at least one polyester of a polyester containing material.

It is another object of the invention to provide a method for degrading at least one polyester of a polyester containing material, wherein the polyester containing material is contacted with an esterase or host cell or extract thereof or composition of the invention, thereby degrading the at least one polyester of a polyester containing material.

Advantageously, polyester(s) is (are) depolymerized up to monomers and/or oligomers.

Particularly, the invention provides a method for degrading PET of a PET containing material, wherein the PET containing material is contacted with an esterase or host cell or composition of the invention, thereby degrading the PET.

In an embodiment, at least one polyester is degraded into repolymerizable monomers and/or oligomers, which may be advantageously retrieved in order to be reused. The retrieved monomers/oligomers may be used for recycling (e.g., repolymerizing polyesters) or methanization. In a particular embodiment, at least one polyester is PET, and monoethylene glycol, terephthalic acid, methyl-2-hydroxyethyl terephthalate (MHET), bis(2-hydroxyethyl) terephthalate (BHET), 1-(2-Hydroxyethyl) 4-methyl terephthalate (HEMT) and/or dimethyl terephthalate (DMT) are retrieved.

In an embodiment, polyester(s) of the polyester containing material is (are) fully degraded.

The time required for degrading a polyester containing material may vary depending on the polyester containing material itself (i.e., nature and origin of the polyester containing material, its composition, shape etc.), the type and amount of esterase used, as well as various process parameters (i.e., temperature, pH, additional agents, etc.). One skilled in the art may easily adapt the process parameters to the polyester containing material and the envisioned degradation time.

Advantageously, the degrading process is implemented at a temperature comprised between 20° C. and preferably between 40° C. and 90° C., more preferably between 50° C. and 70° C. In a particular embodiment, the degrading process is implemented at 60° C. In another particular embodiment, the degrading process is implemented at 65° C. In another particular embodiment, the degrading process is implemented at 70° C. More generally, the temperature is maintained below an inactivating temperature, which corresponds to the temperature at which the esterase is inactivated (i.e., temperature at which the esterase has lost more than 80% of activity as compared to its activity at its optimum temperature) and/or the recombinant microorganism does no more synthesize the esterase. Particularly, the temperature is maintained below the glass transition temperature (Tg) of the targeted polyester.

Advantageously, the process is implemented in a continuous flow process, at a temperature at which the esterase can be used several times and/or recycled.

Advantageously, the degrading process is implemented at a pH comprises between 5 to 9, preferably in a range of pH from 6 to 9, more preferably in a range of pH from 6.5 to 9, even more preferably in a range of pH from 6.5 to 8.

In a particular embodiment, the polyester containing material may be pretreated prior to be contacted with the esterase, in order to physically change its structure, so as to increase the surface of contact between the polyester and the esterase.

It is another object of the invention to provide a method of producing monomers and/or oligomers from a polyester containing material, comprising exposing a polyester containing material to an esterase of the invention, or corresponding recombinant cell or extract thereof, or composition, and optionally recovering monomers and/or oligomers.

Monomers and/or oligomers resulting from the depolymerization may be recovered, sequentially or continuously. A single type of monomers and/or oligomers or several different types of monomers and/or oligomers may be recovered, depending on the starting polyester containing material.

The method of the invention is particularly useful for producing monomers selected from monoethylene glycol and terephthalic acid, and/or oligomers selected from methyl-2-hydroxyethyl terephthalate (MHET), bis(2-hydroxyethyl) terephthalate (BHET), 1-(2-Hydroxyethyl) 4-methyl terephthalate (HEMT) and dimethyl terephthalate (DMT), from PET, and/or plastic product comprising PET.

The recovered monomers and/or oligomers may be further purified, using all suitable purifying methods and conditioned in a re-polymerizable form.

Recovered repolymerizable monomers and/or oligomers may be reused for instance to synthesize polyesters. Advantageously, polyesters of same nature are repolymerized. However, it is possible to mix the recovered monomers and/or oligomers with other monomers and/or oligomers, in order for instance to synthesize new copolymers. Alternatively, the recovered monomers may be used as chemical intermediates in order to produce new chemical compounds of interest.

The invention also relates to a method of surface hydrolysis or surface functionalization of a polyester containing material, comprising exposing a polyester containing material to an esterase of the invention, or corresponding recombinant cell or extract thereof, or composition. The method of the invention is particularly useful for increasing hydrophilicity, or water absorbency, of a polyester material. Such increased hydrophilicity may have particular interest in textiles production, electronics and biomedical applications.

It is a further object of the invention to provide a polyester containing material in which an esterase of the invention and/or a recombinant microorganism expressing and excreting said esterase is/are included. As an example, processes for preparing such polyester containing material including an esterase of the invention are disclosed in the patent applications WO2013/093355, WO2016/198650, WO2016/198652, WO2019/043145 and WO2019/043134.

It is thus an object of the invention to provide a polyester containing material containing an esterase of the invention and/or a recombinant cell and/or a composition or extract thereof and at least PET. According to an embodiment, the invention provides a plastic product comprising PET and an esterase of the invention having a PET degrading activity.

It is thus another object of the invention to provide a polyester containing material containing an esterase of the invention and/or a recombinant cell and/or a composition or extract thereof and at least PBAT. According to an embodiment, the invention provides a plastic product comprising PBAT and an esterase of the invention having a PBAT degrading activity.

It is thus another object of the invention to provide a polyester containing material containing an esterase of the invention and/or a recombinant cell and/or a composition or extract thereof and at least PBS. According to an embodiment, the invention provides a plastic product comprising PBS and an esterase of the invention having a PBS degrading activity.

It is thus another object of the invention to provide a polyester containing material containing an esterase of the invention and/or a recombinant cell and/or a composition or extract thereof and at least PCL. According to an embodiment, the invention provides a plastic product comprising PCL and an esterase of the invention having a PCL degrading activity.

Classically, an esterase of the invention may be used in detergent, food, animal feed, paper making, textile and pharmaceutical applications. More particularly, the esterase of the invention may be used as a component of a detergent composition. Detergent compositions include, without limitation, hand or machine laundry detergent compositions, such as laundry additive composition suitable for pre-treatment of stained fabrics and rinse added fabric softener composition, detergent composition for use in general household hard surface cleaning operations, detergent compositions for hand or machine dishwashing operations. In a particular embodiment, an esterase of the invention may be used as a detergent additive. The invention thus provides detergent compositions comprising an esterase of the invention. Particularly, the esterase of the invention may be used as a detergent additive in order to reduce pilling and greying effects during textile cleaning.

The present invention is also directed to methods for using an esterase of the invention in animal feed, as well as to feed compositions and feed additives comprising an esterase of the invention. The terms "feed" and "feed composition" refer to any compound, preparation, mixture, or composition suitable for, or intended for intake by an animal. In another particular embodiment, the esterase of the invention is used to hydrolyze proteins, and to produce hydrolysates comprising peptides. Such hydrolysates may be used as feed composition or feed additives.

It is a further object of the invention to provide a method for using an esterase of the invention in papermaking industry. More particularly, the esterase of the invention may be used to remove stickies from the paper pulp and water pipelines of paper machines.

EXAMPLES

Example 1—Construction, Expression and Purification of Esterases

Construction

Esterase according to the invention have been generated using the plasmidic construction. This plasmid consists in cloning a gene encoding the esterase of SEQ ID No 1, optimized for *Escherichia coli* expression between NdeI and XhoI restriction sites of a pET-26b(+) expression vector (Merck Millipore, Molsheim, France). A nucleotidic sequence coding for a PelB leader sequence has been added between SEQ ID No 1 and NdeI restriction site. Expressed fusion protein is directed to bacterial periplasm where the PelB leader sequence is removed by a signal peptidase giving a functional protein identical to SEQ ID No 1 but added with a C-terminal amino acid extension. Two site directed mutagenesis kits have been used according to the recommendations of the supplier, in order to generate the esterase variants: QuikChange II Site-Directed Mutagenesis kit and QuikChange Lightning Multi Site-Directed from Agilent (Santa Clara, California, USA).

Expression and Purification of the Esterases

The strains Stellar™ (Clontech, California, USA) and *E. coli* BL21 (DE3) (New England Biolabs, Evry, France) have been successively employed to perform the cloning and recombinant expression in 50 mL LB-Miller medium or ZYM auto inducible medium (Studier et al., 2005-Prot. Exp. Pur. 41, 207-234). The induction in LB-Miller medium has been performed at 16° C., with 0.5 mM of isopropyl β-D-1-thiogalactopyranoside (IPTG, Euromedex, Souffelweyersheim, France). The cultures have been stopped by centrifugation (8000 rpm, 20 minutes at 10° C.) in an Avanti J-26 XP centrifuge (Beckman Coulter, Brea, USA). The cells have been suspended in 20 mL of Talon buffer (Tris-HCl 20 mM, NaCl 300 mM, pH 8). Cell suspension was then sonicated during 2 minutes with 30% of amplitude (2 sec ON and 1 sec OFF cycles) by FB 705 sonicator (Fisherbrand, Illkirch, France). Then, a step of centrifugation has been realized: 30 minutes at 10000 g, 10° C. in an Eppendorf centrifuge. The soluble fraction has been collected and submitted to affinity chromatography. This purification step has been completed with Talon® Metal Affinity Resin (Clontech, CA, USA). Protein elution has been carried out with steps of Talon buffer supplemented with imidazole. Purified protein has been dialyzed against Talon buffer then quantified using Bio-Rad protein assay according to manufacturer instructions (Lifescience Bio-Rad, France) and stored at +4° C.

Example 2—Evaluation of the Degrading Activity of the Esterases

The degrading activity of the esterases has been determined and compared to the activity of esterase of SEQ ID No 1.

Multiple methodologies to assess the specific activity have been used:

(1) Specific activity based upon PET hydrolysis
(2) Activity based upon the degradation of a polyester under solid form
(3) Activity based upon PET hydrolysis in reactors above 100 mL 100 mL 2.1. Specific Activity Based Upon PET Hydrolysis 100 mg of amorphous PET under powder form (prepared according to WO 2017/198786 to reach a crystallinity below 20%) were weighted and introduced in a 100 mL glass bottle. 1 mL of esterase preparation comprising esterase of SEQ ID No 1 (as reference control) or esterase of the invention, prepared at 1.38 μM in Talon buffer (Tris-HCl 20 mM, NaCl 0.3M, pH 8) were introduced in the glass bottle. Finally, 9 mL of 0.1 M potassium phosphate buffer pH 8 were added.

The depolymerization started by incubating each glass bottle at 40° C., 45° C., 50° C., 55° C., 60° C., 65° C. or 70° C. and 150 rpm in a Max Q 4450 incubator (Thermo Fisher Scientific, Inc. Waltham, MA, USA).

The initial rate of depolymerization reaction, in mg of equivalent TA generated/hour, was determined by samplings performed at different time during the first 24 hours and analyzed by Ultra High Performance Liquid Chromatography (UHPLC). If necessary, samples were diluted in 0.1 M potassium phosphate buffer pH 8. Then, 150 μL of methanol and 6.5 μL of HCl 6 N were added to 150 μL of sample or dilution. After mixing and filtering on 0.45 μm syringe filter, samples were loaded on UHPLC to monitor the liberation of terephthalic acid (TA), MHET and BHET. Chromatography system used was an Ultimate 3000 UHPLC system (Thermo Fisher Scientific, Inc. Waltham, MA, USA) including a pump module, an autosampler, a column oven thermostated at 25° C., and an UV detector at 240 nm. The column used was a Discovery® HS C18 HPLC Column (150×4.6 mm, 5 μm, equipped with precolumn, Supelco, Bellefonte, USA). TA, MHET and BHET were separated using a gradient of MeOH (30% to 90%) in 1 mM of $H_2SO_4$ at 1 mL/min. Injection was 20 μL of sample. TA, MHET and BHET were measured according to standard curves prepared from commercial TA and BHET and in house synthetized MHET in the same conditions than samples. The specific activity of PET hydrolysis (mg of equivalent TA/hour/mg of enzyme) was determined in the linear part of the hydrolysis curve of the reaction, such curve being set up by samplings performed at different time during the first 72 hours. Equivalent TA corresponds to the sum of TA measured and of TA contained in measured MHET and BHET. Said measurement of equivalent TA can also be used to calculate the yield of a PET depolymerization assay at a given time.

2.2. Activity Based Upon Degradation of a Polyester Under Solid Form

20 μL of enzyme preparation was deposited in a well created in an agar plate containing PET. Preparation of agar plates was realized by solubilizing 500 mg of PET in hexafluoro-2-propanol (HFIP) and pouring this medium in a 250 mL aqueous solution. After HFIP evaporation at 52° C. under 140 mbar, the solution was mixed v/v with 0.2 M potassium phosphate buffer pH 8 containing 3% agar. Around 30 mL of the mixture is used to prepare each plate and stored at 4° C.

The diameters or the surface area of the halos formed due to the polyester degradation by wild-type esterase and variants were measured and compared after 2 to 24 hours at 40° C., 45° C., 50° C., 55° C., 60° C., or 70° C.

2.3. Activity Based Upon PET Hydrolysis in Reactor

From 0.69 μmol to 2.07 μmol of purified esterase prepared in 80 mL of 100 mM potassium phosphate buffer pH 8 were mixed with 20 g amorphous PET (prepared according to WO 2017/198786 to reach a crystallinity below 20%) in a 500 mL Minibio bioreactor (Applikon Biotechnology, Delft, The Netherlands). Temperature regulation at 40° C., 45° C., 50° C., 55° C., 60° C., 65° C. or 70° C. was performed by water bath immersion and a single marine impeller was used to maintain constant agitation at 250 rpm. The pH of the PET depolymerization assay was regulated at pH 8 by 6N NaOH and was assured by my-Control bio controller system (Applikon Biotechnology, Delft, The Netherlands). Base consumption was recorded during the assay and may be used for the characterization of the PET depolymerization assay.

The final yield of the PET depolymerization assay was determined either by the determination of residual PET weight or by the determination of equivalent TA generated, or through the base consumption. Weight determination of residual PET was assessed by the filtration, at the end of the reaction, of the reactional volume through a 12 to 15 μm grade 11 ashless paper filter (Dutscher SAS, Brumath, France) and drying of such retentate before weighting it. The determination of equivalent TA generated was realized using UHPLC methods described in 2.1, and the percentage of hydrolysis was calculated based on the ratio of molar concentration at a given time (TA+MHET+BHET) versus the total amount of TA contained in the initial sample. PET depolymerization produced acid monomers that will be neutralized with the base to be able to maintain the pH in the reactor. The determination of equivalent TA produced was calculating using the corresponding molar base consumption, and the percentage of hydrolysis was calculated based on the ratio of molar concentration at a given time of equivalent TA versus the total amount of TA contained in the initial sample.

PET depolymerization yield of the esterases (variants) of the invention after 24 hours at 65° C. are shown in Table 1 below. Table 1 indicates the improvement of PET depolymerization yield of the variants of the invention as compared to the PET depolymerization yield of the esterase of SEQ ID No 1 used as reference (whose PET depolymerization yield is considered equal to 1).

The PET depolymerization yield is measured as exposed in Example 2.1.

TABLE 1

Improvement of PET depolymerization yield for an esterase of the invention after 24 hours at 65° C. as compared to the esterase of SEQ ID No1.

| Variants | Improvement of PET depolymerization yield as compared to SEQ ID No1 |
|---|---|
| V1: N204C + S251C | 20.4 times |
| V2: F209I + N204C + S251C + Q94G | 18.2 times |
| V3: F209I + N204C + S251C + Q94G + S214P + T183E | 47.3 times |
| V4: F209I + N204C + S251C + Q94G + S214P + G135A + T168Q + T183E | 16.2 times |

Variants V1-V4 have the exact amino acid sequence as set forth in SEQ ID No1, except the combination of substitutions listed in Table 1, respectively.

Table 1 shows that the PET depolymerization yield at 65° C. of all the variants is at least 16.2 times higher than the PET depolymerization yield of the esterase of SEQ ID No 1.

Specific degrading activity of esterases (variants) of the invention are shown in Table 2 below. The specific degrading activity of the esterase of SEQ ID No 1 is used as a reference and considered as 100% specific degrading activity. The specific degrading activity is measured as exposed in Example 2.1 at 65° C.

TABLE 2

Specific degrading activity of variants of the invention

| Variants | Specific degrading activity |
|---|---|
| V1: N204C + S251C | 416% |
| V2: F209I + N204C + S251C + Q94G | 575% |
| V3: F209I + N204C + S251C + Q94G + S214P + T183E | 1486% |
| V4: F209I + N204C + S251C + Q94G + S214P + G135A + T168Q + T183E | 599% |

Variants V1-V4 have the exact amino acid sequence as set forth in SEQ ID No1, except the combination of substitutions listed in Table 2, respectively.

Example 3—Evaluation of the Thermostability of Esterases of the Invention

The thermostability of esterases of the invention has been determined and compared to the thermostability of the esterase of SEQ ID No 1.

Different methodologies have been used to estimate thermostability:

(1) Circular dichroism of proteins in solution;

(2) Residual esterase activity after protein incubation in given conditions of temperatures, times and buffers;

(3) Residual polyester's depolymerization activity after protein incubation in given conditions of temperatures, times and buffers;

(4) Ability to degrade a solid polyester compound (such as PET or PBAT or analogues) dispersed in an agar plate, after protein incubation in given conditions of temperatures, times and buffers;

(5) Ability to perform multiple rounds of polyester's depolymerization assays in given conditions of temperatures, buffers, protein concentrations and polyester concentrations;

(6) Differential Scanning Fluorimetry (DSF).

Details on the protocol of such methods are given below.

3.1 Circular Dichroism

Circular dichroism (CD) has been performed with a Jasco 815 device (Easton, USA) to compare the melting temperature (T m) of the esterase of SEQ ID No 1 with the Tm of the esterases of the invention. Technically 4004 protein sample was prepared at 0.5 mg/mL in Talon buffer and used for CD. A first scan from 280 to 190 nm was realized to determine two maxima intensities of CD corresponding to the correct folding of the protein. A second scan was then performed from 25° C. to 110° C., at length waves corresponding to such maximal intensities and providing specific curves (sigmoid 3 parameters y=a/(1+e^((x−x0)/b))) that were analyzed by Sigmaplot version 11.0 software, the Tm is determined when x=x0. The $T_m$ obtained reflects the thermostability of the given protein. The higher the $T_m$ is, the more stable the variant is at high temperature.

3.2 Residual Esterase Activity 1 mL of a solution of 40 mg/L (in Talon buffer) of the esterase of SEQ ID No 1 or of an esterase of the invention was incubated at different temperatures (40, 50, 60, 65, 70, 75, 80 and 90° C.) up to 10 days. Regularly, a sample, was taken, diluted 1 to 500 times in a 0.1M potassium phosphate buffer pH 8.0 and para nitro phenol-butyrate (pNP-B) assay was realized. 20 μL of sample are mixed with 175 μL of 0.1M potassium phosphate buffer pH 8.0 and 5 μL of pNP-B solution in 2-methyl-2 butanol (40 mM). Enzymatic reaction was performed at 30° C. under agitation, during 15 minutes and absorbance at 405 nm was acquired by microplate spectrophotometer (Versamax, Molecular Devices, Sunnyvale, CA, USA). Activity of pNP-B hydrolysis (initial velocity expressed in μmol of pNPB/min) was determined using a standard curve for the liberated para nitro phenol in the linear part of the hydrolysis curve.

3.3 Residual Polyester Depolymerizing Activity 10 mL of a solution of 40 mg/L (in Talon buffer) of the esterase of SEQ ID No 1 and of an esterase of the invention respectively were incubated at different temperatures (40° C., 50° C., 60° C., 65° C., 70° C., 75° C., 80° C. and 90° C.) up to 30 days. Regularly, a 1 mL sample was taken, and transferred into a bottle containing 100 mg of amorphous PET (prepared according to WO 2017/198786 to reach a crystallinity below 20%) micronized at 250-500 μm and 49 mL of 0.1M potassium phosphate buffer pH 8.0 and incubated at 50° C., 55° C., 60° C., 65° C. or 70° C. 150 μL of buffer were sampled regularly. When required, samples were diluted in 0.1 M potassium phosphate buffer pH 8. Then, 150 μL of methanol and 6.5 μL of HCl 6 N were added to 150 μL of sample or dilution. After mixing and filtering on 0.45 μm syringe filter, samples were loaded on UHPLC to monitor the liberation of terephthalic acid (TA), MHET and BHET. Chromatography system used was an Ultimate 3000 UHPLC system (Thermo Fisher Scientific, Inc. Waltham, MA, USA) including a pump module, an autosampler, a column oven thermostated at and an UV detector at 240 nm. The column used was a Discovery® HS C18 HPLC Column (150×4.6 mm, 5 μm, equipped with precolumn, Supelco, Bellefonte, USA). TA, MHET and BHET were separated using a gradient of MeOH (30% to 90%) in 1 mM of $H_2SO_4$ at 1 mL/min. Injection was 20 μL of sample. TA, MHET and BHET were measured according to standard curves prepared from commercial TA and BHET and in house synthetized MHET in the same conditions than samples. Activity of PET hydrolysis (μmol of PET hydrolysed/min or mg of equivalent TA produced/hour) was determined in the linear part of the hydrolysis curve, such curve being set up by samplings performed at different time during the first 24 hours. Equivalent TA corresponds to the sum of TA measured and of TA contained in measured MHET and BHET.

3.4 Degradation of a Polyester Under Solid Form 1 mL of a solution of 40 mg/L (in Talon buffer) of the esterase of SEQ ID No 1 and of an esterase of the invention respectively were incubated at different temperatures (40° C., 50° C., 60° C., 65° C., 70° C., 75° C., and 90° C.) up to 30 days. Regularly, 20 μL of enzyme preparation was deposited in a well created in an agar plate containing PET. Preparation of agar plates containing PET was realized by solubilizing 500 mg of PET in hexafluoro-2-propanol (HFIP), and pouring this medium in a 250 mL aqueous solution. After HFIP evaporation at 52° C. under 140 mbar, the solution was mixed v/v with 0.2 M potassium phosphate buffer pH 8 containing 3% agar. Around 30 mL of the mixture is used to prepare each omnitray and stored at 4° C.

The diameter or the surface area of the halos formed due to the polyester degradation by wild-type esterase and variants of the invention were measured and compared after 2 to 24 hours at 50° C., 55° C., 65° C. or 70° C. The half-life of the enzyme at a given temperature corresponds to the time required to decrease by a 2-fold factor the diameter of the halo.

3.5 Multiple Rounds of Polyester's Depolymerization

The ability of the esterase to perform successive rounds of polyester's depolymerization assays was evaluated in an enzymatic reactor. A Minibio 500 bioreactor (Applikon Biotechnology B. V., Delft, The Netherlands) was started with 3 g of amorphous PET (prepared according to WO 2017/198786 to reach a crystallinity below 20%) and 100 mL of 10 mM potassium phosphate buffer pH 8 containing 3 mg of esterase. Agitation was set at 250 rpm using a marine impeller. Bioreactor was thermostated at 50° C., 55° C., 60° C., 65° C. or 70° C. by immersion in an external water bath. pH was regulated at 8 by addition of KOH at 3 M. The different parameters (pH, temperature, agitation, addition of base) were monitored thanks to BioXpert software V2.95. 1.8 g of amorphous PET (prepared according to WO 2017/198786 to reach a crystallinity below 20%) were added every 20 h. 500 μL of reaction medium was sampled regularly.

Amount of TA, MHET and BHET was determined by HPLC, as described in example 2.3. Amount of EG was determined using an Aminex HPX-87K column (Bio-Rad Laboratories, Inc, Hercules, California, United States) thermostated at 65° C. Eluent was $K_2HPO_4$ 5 mM at 0.6 $mL\cdot min^{-1}$. Injection was 20 μL. Ethylene glycol was monitored using refractometer.

The percentages of hydrolysis were calculated based on the ratio of molar concentration at a given time (TA+

MHET+BHET) versus the total amount of TA contained in the initial sample, or based on the ratio of molar concentration at a given time (EG+MHET+2×BHET) versus the total amount of EG contained in the initial sample. Rate of degradation is calculated in mg of total liberated TA per hour or in mg of total EG per hour.

Half-life of enzyme was evaluated as the incubation time required to obtain a loss of 50% of the degradation rate.

3.6 Differential Scanning Fluorimetry (DSF)

DSF was used to evaluate the thermostability of the wild-type protein (SEQ ID No 1) and variants thereof by determining their melting temperature (Tm), temperature at which half of the protein population is unfolded. Protein samples were prepared at a concentration of 14 μM and stored in buffer A consisting of 20 mM Tris HCl pH 8.0, 300 mM NaCl. The SYPRO orange dye 5000× stock solution in DMSO was first diluted to 250× in water. Protein samples were loaded onto a white clear 96-well PCR plate (Bio-Rad cat #HSP9601) with each well containing a final volume of 25 μl. The final concentration of protein and SYPRO Orange dye in each well were 5 μM (0.14 mg/ml) and 10× respectively. Loaded volumes per well were as follow: 15 μL of buffer A, 9 μL of the 14 μM protein solution and 1 μL of the 250× Sypro Orange diluted solution. The PCR plates were then sealed with optical quality sealing tape and spun at 2000 rpm for 1 min at room temperature. DSF experiments were then carried out using a CFX96 real-time PCR system set to use the 450/490 excitation and 560/580 emission filters. The samples were heated from 25 to 100° C. at the rate of 0.3° C./second. A single fluorescence measurement was taken every 0.03 second. Melting temperatures were determined from the peak(s) of the first derivatives of the melting curve using the Bio-Rad CFX Manager software.

Esterase of SEQ ID No 1 and esterases of the invention were then compared based on their Tm values. Due to high reproducibility between experiments on the same protein from different productions, a ΔTm of 0.8° C. was considered as significant to compare variants. Tm values correspond to the average of at least 3 measurements.

Tm of the esterase of SEQ ID No 1 is estimated to 63.1° C.+/−0.4° C. as exposed in Example 3.6.

Thermostabilities of esterase variants of the invention are shown in Table 3 below, expressed in Tm values and evaluated according to Example 3.6. The gain of Tm as compared to the esterase of SEQ ID No 1 is indicated in brackets.

TABLE 3

Tm of the esterases of the invention

| Variants | Tm |
|---|---|
| V1: N204C + S251C | 73.6° C. (+10.5° C.) |
| V2: F209I + N204C + S251C + Q94G | 72.8° C. (+9.7° C.) |
| V3: F209I + N204C + S251C + Q94G + S214P + T183E | 77.5° C. (+14.4° C.) |
| V4: F209I + N204C + S251C + Q94G + S214P + G135A + T168Q + T183E | 65.2° C. (+2.1° C.) |

Variants V1-V4 have the exact amino acid sequence as set forth in SEQ ID No1, except the combination of substitutions listed in Table 3, respectively.

The invention claimed is:

1. An esterase which (i) has at least 90% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

2. The esterase according to claim 1, wherein said esterase further comprises at least a substitution at position F209 selected from F209A/G/H/L/N/R/S/T/M or F209I/W.

3. The esterase according to claim 1, wherein said esterase further comprises at least one substitution selected from T63M/V, S67T, Q94G/P/N/T/Y, G135A, T168Q/V, S177H/Q/N, T183E, F209I/W/A/G/H/L/N/R/S/T/M, Q212D/M and S214P/D.

4. The esterase according to claim 1, wherein the esterase further comprises at least one, two or three additional amino acid substitutions selected from T63M/V, S67T, Q94G/P/N/T/Y, G135A, T168Q/V, S177H/Q/N, T183E, F209I/W/A/G/H/L/N/R/S/T/M, Q212D/M and S214P/D.

5. The esterase according to claim 1, wherein said esterase comprises a combination of substitutions selected from F209A/G/H/L/N/R/S/T/M+N204C+S251C+Q94G/P, F209I/W+N204C+S251C+Q94G, or F209I+N204C+S251C+Q94G.

6. The esterase according to claim 1, wherein said esterase comprises at least a combination of substitutions selected from F209I/W/A/G/H/L/N/R/S/T/M+N204C+S251C, F209I/W/A/G/H/L/N/R/S/T/M+N204C+S251C+Q94G/P, F209I/W/A/G/H/L/N/R/S/T/M+N204C+S251C+Q212D/M, F209I/W/A/G/H/L/N/R/S/T/M+N204C+S251C+Q94G/P+S214P/D+G135A+T168Q, F209I/W/A/G/H/L/N/R/S/T/M+N204C+S251C+Q94G/P+S214P/D+G135A+T168Q+T183E, F209I/W/A/G/H/L/N/R/S/T/M+N204C+S251C+Q94G/P+S214P/D+T183E and F209I/W/A/G/H/L/N/R/S/T/M+N204C+S251C+Q94G/P+S214P/D+T183E+T168Q.

7. The esterase according to claim 1, wherein said the amino acid sequence of the esterase consists of the amino acid sequence as set forth in SEQ ID NO: 1 with a combination of substitutions selected from N204C+S251C, F209I/W/A/G/H/L/N/R/S/T/M+N204C+S251C, F209I/W/A/G/H/L/N/R/S/T/M+N204C+S251C+Q94G/P, F209I/W/A/G/H/L/N/R/S/T/M+N204C+S251C+Q212D/M, F209I/W/A/G/H/L/N/R/S/T/M+N204C+S251C+Q94G/P+S214P/D+G135A+T168Q, F209I/W/A/G/H/L/N/R/S/T/M+N204C+S251C+Q94G/P+S214P/D+G135A+T168Q+T183E, F209I/W/A/G/H/L/N/R/S/T/M+N204C+S251C+Q94G/P+S214P/D+T183E and F209I/W/A/G/H/L/N/R/S/T/M+N204C+S251C+Q94G/P+S214P/D+T183E+T168Q.

8. The esterase according to claim 1, wherein said esterase comprises at least one amino acid residue selected from C241, C257, E174, S130, D176, H208, G61, F62, M131, A70, T136, H129, G132, W155, 1171, 1178, R91, T217 and S65 as set forth in SEQ ID NO: 1.

9. The esterase according to claim 1, wherein said esterase comprises at least one amino acid residue selected from A70, T136, H129, G132, W155, 1171, I178, R91, T217 and S65 as set forth in SEQ ID NO: 1.

10. The esterase according to claim 1, wherein said esterase exhibits both an increased thermostability and an increased degrading activity as compared to the esterase of SEQ ID NO: 1.

11. A nucleic acid encoding an esterase according to claim 1, an expression cassette or vector comprising said nucleic acid, or a host cell comprising said nucleic acid.

12. A composition comprising an esterase according to claim 1.

13. A method of degrading a polyester comprising (a) contacting the polyester with an esterase according to claim 1 or a host cell comprising said esterase; and, optionally (b) recovering monomers and/or oligomers.

14. A polyester containing material containing an esterase according to claim 1.

15. A detergent composition comprising the esterase according to claim 1.

16. The esterase according to claim 1, wherein said esterase comprises at least a combination of substitutions selected from N204C+S251C, F209I+N204C+S251C+Q94G, F209I+N204C+S251C+Q94G+S214P+T183E and F209I+N204C+S251C+Q94G+S214P+G135A+T168Q+T183E.

17. The esterase according to claim 1, wherein said the amino acid sequence of the esterase consists of the amino acid sequence as set forth in SEQ ID NO: 1 with a single combination of substitutions selected from N204C+S251C, F209I+N204C+S251C+Q94G, F209I+N204C+S251C+Q94G+S214P+T183E and F209I+N204C+S251C+Q94G+S214P+G135A+T168Q+T183E.

18. The esterase according to claim 1, wherein said esterase comprises at least one amino acid residue selected from C241, C257, E174, S130, D176, H208, G61, F62, M131, A70, T136, H129, G132, W155, 1171, 1178, R91, T217 and S65 as set forth in SEQ ID NO: 1.

19. The esterase according to claim 1, wherein said esterase comprises at least one amino acid residue selected from A70, T136, H129, G132, W155, 1171, 1178, R91, T217 and S65 as set forth in SEQ ID NO: 1.

20. The esterase according to claim 1, wherein said esterase (i) has at least 95% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

21. The esterase according to claim 1, wherein said esterase (i) has at least 96% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

22. The esterase according to claim 1, wherein said esterase (i) has at least 97% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

23. The esterase according to claim 1, wherein said esterase (i) has at least 98% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

24. The esterase according to claim 1, wherein said esterase (i) has at least 99% identity to the full length amino acid sequence set forth in SEQ ID NO: 1, and (ii) comprises at least the combination of substitutions N204C+S251C wherein the positions are numbered by reference to the amino acid sequence set forth in SEQ ID NO: 1, (iii) has a polyester degrading activity and (iv) exhibits an increased thermostability and/or an increased degrading activity compared to the esterase of SEQ ID NO: 1.

25. The esterase according to claim 1, wherein said esterase comprises the combination of substitutions N204C+S251C wherein the positions are numbered by reference to the amino acid sequence set forth in SEQ ID NO: 1 and said esterase has increased thermostability and increased degrading activity compared to the esterase of SEQ ID NO: 1.

* * * * *

SEQUENCE LISTING

```
<160> NUMBER OF SEQ ID NOS: 1

<210> SEQ ID NO 1
<211> LENGTH: 260
<212> TYPE: PRT
<213> ORGANISM: Thermomonospora curvata

<400> SEQUENCE: 1

Ala Asn Pro Tyr Gln Arg Gly Pro Asp Pro Thr Glu Ser Leu Leu Arg
1               5                   10                  15

Ala Ala Arg Gly Pro Phe Ala Val Ser Glu Gln Ser Val Ser Arg Leu
            20                  25                  30

Ser Val Ser Gly Phe Gly Gly Gly Arg Ile Tyr Tyr Pro Thr Thr Thr
        35                  40                  45

Ser Gln Gly Thr Phe Gly Ala Ile Ala Ile Ser Pro Gly Phe Thr Ala
    50                  55                  60

Ser Trp Ser Ser Leu Ala Trp Leu Gly Pro Arg Leu Ala Ser His Gly
65                  70                  75                  80

Phe Val Val Ile Gly Ile Glu Thr Asn Thr Arg Leu Asp Gln Pro Asp
                85                  90                  95

Ser Arg Gly Arg Gln Leu Leu Ala Ala Leu Asp Tyr Leu Thr Gln Arg
            100                 105                 110

Ser Ser Val Arg Asn Arg Val Asp Ala Ser Arg Leu Ala Val Ala Gly
        115                 120                 125

His Ser Met Gly Gly Gly Gly Thr Leu Glu Ala Ala Lys Ser Arg Thr
    130                 135                 140

Ser Leu Lys Ala Ala Ile Pro Ile Ala Pro Trp Asn Leu Asp Lys Thr
145                 150                 155                 160

Trp Pro Glu Val Arg Thr Pro Thr Leu Ile Ile Gly Gly Glu Leu Asp
```

-continued

```
                165                 170                 175

Ser Ile Ala Pro Val Ala Thr His Ser Ile Pro Phe Tyr Asn Ser Leu
            180                 185                 190

Thr Asn Ala Arg Glu Lys Ala Tyr Leu Glu Leu Asn Asn Ala Ser His
        195                 200                 205

Phe Phe Pro Gln Phe Ser Asn Asp Thr Met Ala Lys Phe Met Ile Ser
    210                 215                 220

Trp Met Lys Arg Phe Ile Asp Asp Asp Thr Arg Tyr Asp Gln Phe Leu
225                 230                 235                 240

Cys Pro Pro Pro Arg Ala Ile Gly Asp Ile Ser Asp Tyr Arg Asp Thr
                245                 250                 255

Cys Pro His Thr
            260
```